(12) United States Patent
Hong et al.

(10) Patent No.: US 9,993,218 B2
(45) Date of Patent: Jun. 12, 2018

(54) METHOD FOR PROJECTION AND BACK-PROJECTION FOR IMAGE PROCESSING, AND IMAGE PROCESSING APPARATUS THEREFOR

(71) Applicant: SAMSUNG ELECTRONICS CO., LTD., Suwon-si (KR)

(72) Inventors: Yoon-mi Hong, Yongin-si (KR); Gye-hyun Kim, Seoul (KR); Jae-sung Lee, Seongnam-si (KR); Jae-chool Lee, Suwon-si (KR); Hae-kyung Jung, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 14/778,864

(22) PCT Filed: Mar. 20, 2014

(86) PCT No.: PCT/KR2014/002334
§ 371 (c)(1),
(2) Date: Sep. 21, 2015

(87) PCT Pub. No.: WO2014/148828
PCT Pub. Date: Sep. 25, 2014

(65) Prior Publication Data
US 2016/0045181 A1 Feb. 18, 2016

(30) Foreign Application Priority Data

Mar. 20, 2013 (KR) ........................ 10-2013-0029925

(51) Int. Cl.
*A61B 6/03* (2006.01)
*A61B 6/00* (2006.01)
*G06T 11/00* (2006.01)

(52) U.S. Cl.
CPC ............ *A61B 6/5258* (2013.01); *A61B 6/032* (2013.01); *A61B 6/4233* (2013.01); *A61B 6/52* (2013.01);
(Continued)

(58) Field of Classification Search
CPC ......... A61B 6/032; A61B 6/4233; A61B 6/52; A61B 6/5205; A61B 6/5258
(Continued)

(56) References Cited

U.S. PATENT DOCUMENTS 5,708,691 A * 1/1998 Zmora ................... A61B 6/032
378/4
5,825,842 A * 10/1998 Taguchi ................. A61B 6/032
378/15
(Continued)

FOREIGN PATENT DOCUMENTS

KR 1020070092006 A 9/2007
KR 1020110083153 A 7/2011
(Continued)

OTHER PUBLICATIONS

Long, et al., "3D Forward and Back-Projection for X-Ray CT Using Separable Footprints", IEEE Transactions on Medical Imaging, vol. 29, Issue No. 11, Nov. 2010, pp. 1839-1850, XP 011336795.
(Continued)

*Primary Examiner* — Allen C. Ho
(74) *Attorney, Agent, or Firm* — Sughrue Mion, PLLC

(57) ABSTRACT

An image processing method of an image processing apparatus includes projecting centers of pixels of a pixel grid onto a preset common axis, mapping a boundary of a detector cell comprised in the detection unit on the preset common axis, and determining a detector value based on the
(Continued)

projecting the centers of the pixels onto the preset common axis and the mapping the boundary of the detector cell on the preset common axis.

21 Claims, 8 Drawing Sheets

(52) U.S. Cl.
CPC .......... *A61B 6/5205* (2013.01); *G06T 11/006* (2013.01); *G06T 2211/424* (2013.01)

(58) Field of Classification Search
USPC .............................. 378/4, 210, 901; 382/131
See application file for complete search history.

(56) References Cited

U.S. PATENT DOCUMENTS

| | | | | |
|---|---|---|---|---|
| 6,307,908 | B1 * | 10/2001 | Hu | G06T 11/005 378/15 |
| 6,314,160 | B1 | 11/2001 | Dhawale et al. | |
| 6,665,369 | B2 * | 12/2003 | Ukita | G06T 11/006 378/4 |
| 6,724,856 | B2 * | 4/2004 | De Man | G06T 11/006 378/62 |
| 7,227,982 | B2 * | 6/2007 | De Man | G06T 11/006 378/62 |
| 7,272,205 | B2 * | 9/2007 | Thibault | A61B 6/032 378/4 |
| 7,529,402 | B2 * | 5/2009 | Ishii | G06T 11/005 345/419 |
| 7,583,780 | B2 * | 9/2009 | Hsieh | A61B 6/032 378/4 |
| 7,778,392 | B1 * | 8/2010 | Berman | A61B 6/032 378/210 |
| 7,920,751 | B2 * | 4/2011 | Li | G01T 1/2985 250/200 |
| 8,116,426 | B2 * | 2/2012 | Hein | G06T 11/005 378/19 |
| 8,121,246 | B2 * | 2/2012 | Morita | G06T 11/005 378/4 |
| 8,135,186 | B2 * | 3/2012 | Bouman | G06T 11/006 378/19 |
| 8,351,574 | B2 * | 1/2013 | Takemoto | A61B 5/02007 378/4 |
| 8,503,750 | B2 * | 8/2013 | Benson | A61B 6/5258 378/4 |
| 8,559,691 | B2 * | 10/2013 | Borghese | G06T 11/006 378/62 |
| 8,649,587 | B2 * | 2/2014 | Star-Lack | G06T 7/0012 378/7 |
| 8,699,811 | B2 * | 4/2014 | Li | G01T 1/2985 250/200 |
| 8,712,121 | B2 * | 4/2014 | Wiegert | A61B 6/032 378/4 |
| 8,731,265 | B2 * | 5/2014 | Nakanishi | A61B 6/032 378/4 |
| 8,913,805 | B2 * | 12/2014 | Long | G06T 11/006 382/128 |
| 8,923,589 | B2 * | 12/2014 | Noda | G06T 11/006 382/131 |
| 8,964,933 | B2 * | 2/2015 | Nakanishi | A61B 6/032 378/4 |
| 8,972,191 | B2 * | 3/2015 | Stampanoni | A61B 6/00 702/1 |
| 9,532,755 | B2 * | 1/2017 | Choi, II | A61B 6/14 |
| 9,848,844 | B2 * | 12/2017 | Simon | A61B 6/5258 |
| 9,861,332 | B2 * | 1/2018 | Fukuda | A61B 6/5205 |
| 2012/0041679 | A1 | 2/2012 | Stampanoni et al. | |
| 2012/0307960 | A1 | 12/2012 | Choi et al. | |

FOREIGN PATENT DOCUMENTS

| | | |
|---|---|---|
| KR | 1020110091354 A | 8/2011 |
| WO | 2010089319 A1 | 8/2010 |
| WO | 2012/069964 A1 | 5/2012 |

OTHER PUBLICATIONS

De Man, et al., "Distance-driven projection and backprojection in three dimensions", Physics in Medicine and Biology, vol. 49, Issue No. 11, Jun. 7, 2004, pp. 2463-2475, XP 020023744.
Communication dated Oct. 4, 2016, issued by the European Patent Office in counterpart European Patent Application No. 14767386.7.
Communication dated Jun. 11, 2014, issued by the International Searching Authority in counterpart International Application No. PCT/KR2014/002334 (PCT/ISA/210 & 237).

* cited by examiner

METHOD FOR PROJECTION AND BACK-PROJECTION FOR IMAGE PROCESSING, AND IMAGE PROCESSING APPARATUS THEREFOR

TECHNICAL FIELD

The present invention relates to an image processing method, an image processing apparatus, and a method for projection and back-projection, and more particularly, to a method for projection and back-projection for minimizing an artifact occurring in an image.

BACKGROUND ART

A projection image may be acquired from an electromagnetic wave that penetrates from a source generating the electromagnetic wave through an object, through a detection unit. Also, a tomography image may be reconstituted through a back-projection method for the acquired projection image.

A detector value is calculated from a pixel when performing a projection, but the pixel value is inferred from the detector value when performing a back-projection. A process of estimating the detector value and the pixel value is required in this process.

However, in projection and back-projection processes, a plurality of pixels included in a pixel grid contribute to a plurality of detector cells included in the detector unit, and thus an artifact exists in comparison with an original image.

Therefore, there is a need for projection and back-projection methods that accurately reflect a contribution of each pixel value to a detector value and a contribution of each detector value to a pixel value.

DETAILED DESCRIPTION OF THE INVENTION

Technical Problem

The present invention provides an image processing method and an image processing apparatus for minimizing artifacts occurring when performing a projection and a back-projection to acquire the same image as an original image.

Technical Solution

According to an aspect of the present invention, there is provided an image processing method of an image processing apparatus, including: projecting centers of pixels of a pixel grid onto a preset common axis; mapping a boundary of a detector cell comprised in a detection unit on the preset common axis; and determining a detector value based on the projecting of the centers of the pixels onto the preset common axis and the mapping of the boundary of the detector cell on the preset common axis.

BEST MODE

Figure 1:
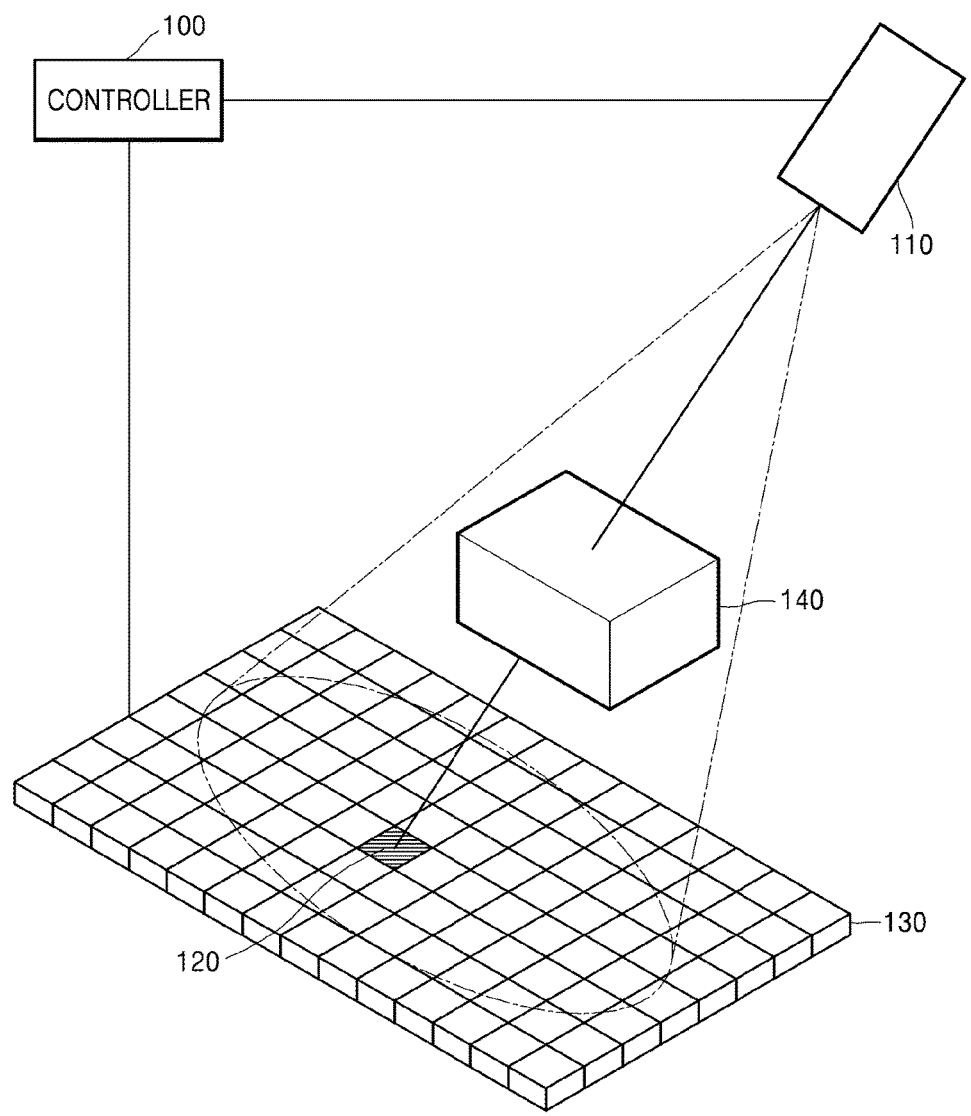
FIG. 1 illustrates an electromagnetic wave that is irradiated from an image photographing system toward an object and passes through the object to reach a detection unit.

According to an aspect of the present invention, there is provided an image processing method of an image processing apparatus, including: projecting centers of pixels of a pixel grid onto a preset common axis; mapping a boundary of a detector cell comprised in a detection unit on the preset common axis; and determining a detector value based on the projecting of the centers of the pixels onto the preset common axis and the mapping of the boundary of the detector cell on the preset common axis.

According to another exemplary embodiment of the present invention, the detector value may be determined by using an equation for integrating a pixel value between points at which the boundary of the detector cell is mapped on the common axis.

According to another exemplary embodiment of the present invention, the determining of the detector value may include determining a pixel value corresponding a point at which the boundary of the detector cell is mapped on the common axis, based on an interpolation.

According to another exemplary embodiment of the present invention, the common axis may be determined according to an angle between a line connecting a source and the detection unit and a horizontal axis.

According to another exemplary embodiment of the present invention, the detector value may be determined based on a partial linear model of a value of the pixel contributing to the detector cell.

According to another aspect of the present invention, there is provided an image processing method of an image processing apparatus, including: projecting a center of a detector cell comprised in a detection unit onto a common axis; mapping a boundary of pixels of a pixel grid on the common axis; and determining a pixel value based on the projecting of the center of the detector cell included in the detection unit onto the preset common axis and the mapping of the boundary of the pixels on the preset common axis.

According to another exemplary embodiment of the present invention, the pixel value may be determined by using an equation for integrating a detector value between points at which the boundary of the pixel is mapped on the common axis.

According to another exemplary embodiment of the present invention, the determining of the pixel value may include determining a detector value corresponding to a point at which the boundary of the pixel is mapped on the common axis, based on an interpolation.

According to another exemplary embodiment of the present invention, the common axis may be determined according to an angle between a line connecting a source and the detection unit and a horizontal axis.

According to another exemplary embodiment of the present invention, the pixel value may be determined based on a partial linear model of a value of the detector cell contributing to a pixel.

According to another aspect of the present invention, there is provided an image processing apparatus including: a source configured to generate an electromagnetic wave; a detection unit configured to include a detector cell detecting the electromagnetic wave; and a controller configured to project centers of pixels of a pixel grid onto a preset common axis, map a boundary of the detector cell on the preset common axis, and determine a detector value by using the projecting result and the mapping result.

According to another exemplary embodiment of the present invention, the controller may determine the detector value by using an equation for integrating a pixel value between points at which the boundary of the detector cell is mapped on the common axis.

According to another exemplary embodiment of the present invention, the controller may determine a detector value corresponding to a point at which a boundary of the detector cell is mapped on the common axis, based on an interpolation.

According to another exemplary embodiment of the present invention, the controller may determine the common axis according to an angle between a line connecting the source and the detection unit and a horizontal axis.

According to another exemplary embodiment of the present invention, the controller may determine the detector value based on a partial linear model of a value of the pixel contributing to the detector cell.

According to another aspect of the present invention, there is provided an image processing apparatus including: a source configured to generate an electromagnetic wave; a detection unit configured to include a detector cell detecting the electromagnetic wave; and a controller configured to project a center of the detector cell onto a preset common axis, map a boundary of pixels of a pixel grid on the preset common axis, and determine a pixel value by using the projection result and the mapping result.

According to another exemplary embodiment of the present invention, the controller may determine the pixel value by using an equation for integrating a detector value between points at which the boundary of the pixel is mapped on the common axis.

According to another exemplary embodiment of the present invention, the controller may determine a detector value corresponding to a point at which the boundary of the pixel is mapped on the common axis, based on an interpolation.

According to another exemplary embodiment of the present invention, the controller may determine the common axis according to an angle between a line connecting the source and the detection unit and a horizontal axis.

According to another exemplary embodiment of the present invention, the controller may determine the pixel value based on a partial linear model of a value of the pixel contributing the detector cell.

A recording medium according to an exemplary embodiment of the present invention may be a non-transitory computer-readable recording medium having recorded thereon a program for performing the method.

MODE OF THE INVENTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

It will be understood that when any part is referred to as being "connected to" or "coupled to" another part, it may be directly connected or coupled to the other element or intervening elements may be present. In contrast, when any part is referred to as including any element, it may further include other elements without excluding other elements.

The present invention provides a method of performing a projection and a back-projection in an image processing method and an image processing apparatus. For example, the present invention provides projection and back-projection methods performed when restoring a sectional image from an x-ray projection image in a computer tomography apparatus.

The present invention will now be described in detail with reference to the attached drawings.

FIG. 1 illustrates an electromagnetic wave that is irradiated from an image photographing system toward an object and passes through the object to reach a detection unit.

An image processing apparatus according to an exemplary embodiment of the present invention may include a source 110 that generates an electromagnetic wave, a detection unit 130 that includes a plurality of detector cells 120 detecting the electromagnetic wave irradiated from the source 110 and generate the electromagnetic wave as an electric signal, and a controller 100 that controls the elements.

The source 110, for example, irradiates an electromagnetic wave such as an x-ray onto an object 140. The electromagnetic wave irradiated from the source 110 may be a fan-beam or a cone-beam, but the present invention is not limited thereto.

The electromagnetic wave passing through the object 140 reaches a detection unit 130, and the detection unit 130 may be divided into the plurality of detector cells 120. The image processing apparatus may detect the electromagnetic wave passing through the object 140 and then reaching the plurality of detector cells 120 to acquire information of the object 140.

The controller 100 may form an image based on the information acquired by the detection unit 130. In other words, the controller 100 may perform a back-projection on a filtered image, which is acquired by an additional post-processing step on a projection image acquired by rotating around each single layer, to generate a final image.

Here, the controller 100 may perform an operation according to a forward projection and a back-projection to form an image. The controller 100 may calculate a pixel value or a detector value for the forward projection and the back projection.

The controller 100 may include at least one processor for performing an operation process.

Figure 2:
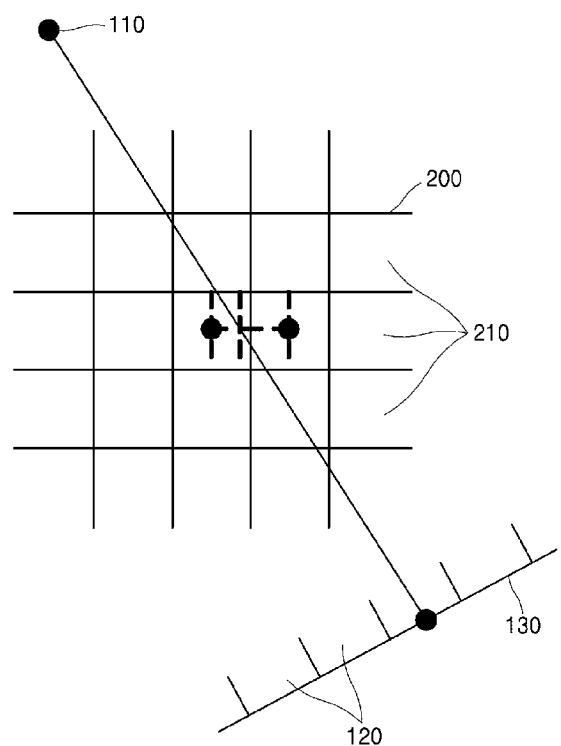
FIG. 2 illustrates a structure for calculating a pixel value when perform image processing according to a first projection method.

FIG. 2 illustrates a structure for calculating a pixel value when performing image processing according to a first projection method.

The first projection method may be referred to as a ray-driven method.

According to the first projection method, for an electromagnetic wave beam that is irradiated from the source 110 and then irradiated in a center of the plurality of detector cells 120 of the detection unit 130 through pixels 210 included in a pixel grid 200, a pixel value between two pixels is calculated through a linear interpolation.

Figure 3:
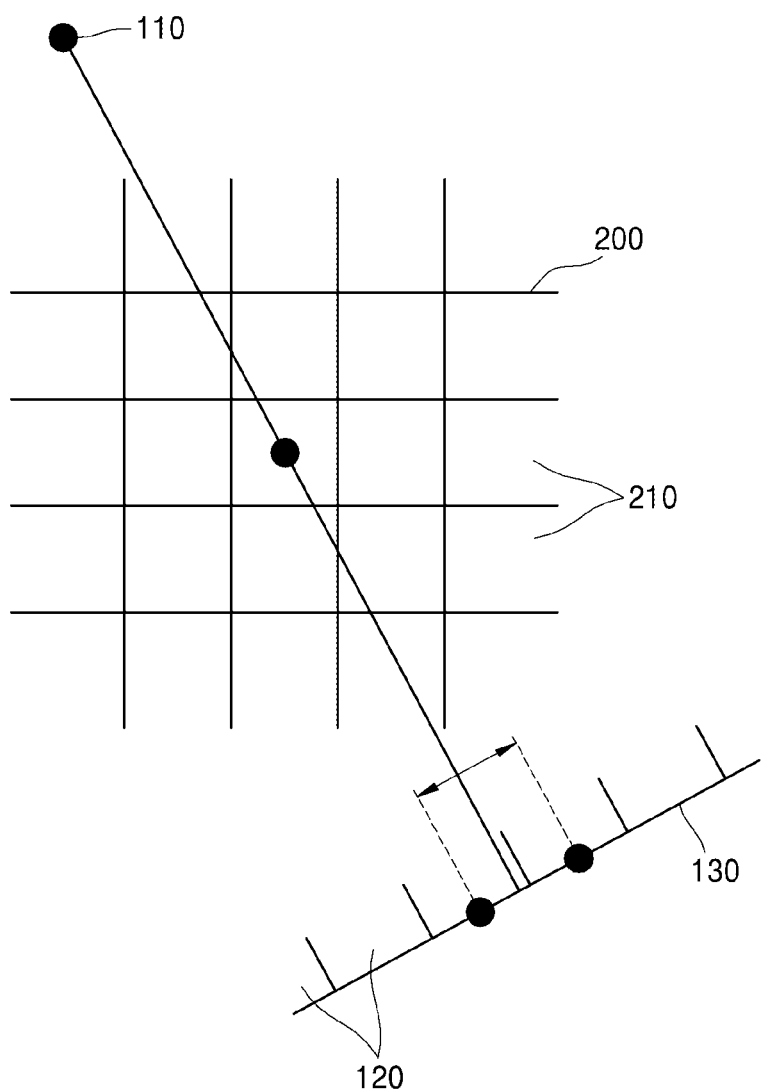
FIG. 3 illustrates a structure for calculating a detector value when performing image processing according to a second projection method.

FIG. 3 illustrates a structure for calculating a detector value when performing image processing according to a second projection method.

The second projection method may be referred to as a pixel-driven method.

According to the second projection method, for an electromagnetic wave beam that is irradiated from the source 110 and then irradiated on the detection unit 130 through a center of the pixels 210 included in the pixel grid 200, a detector value for an adjacent detector cell 120 is calculated through a linear interpolation.

Figure 4:
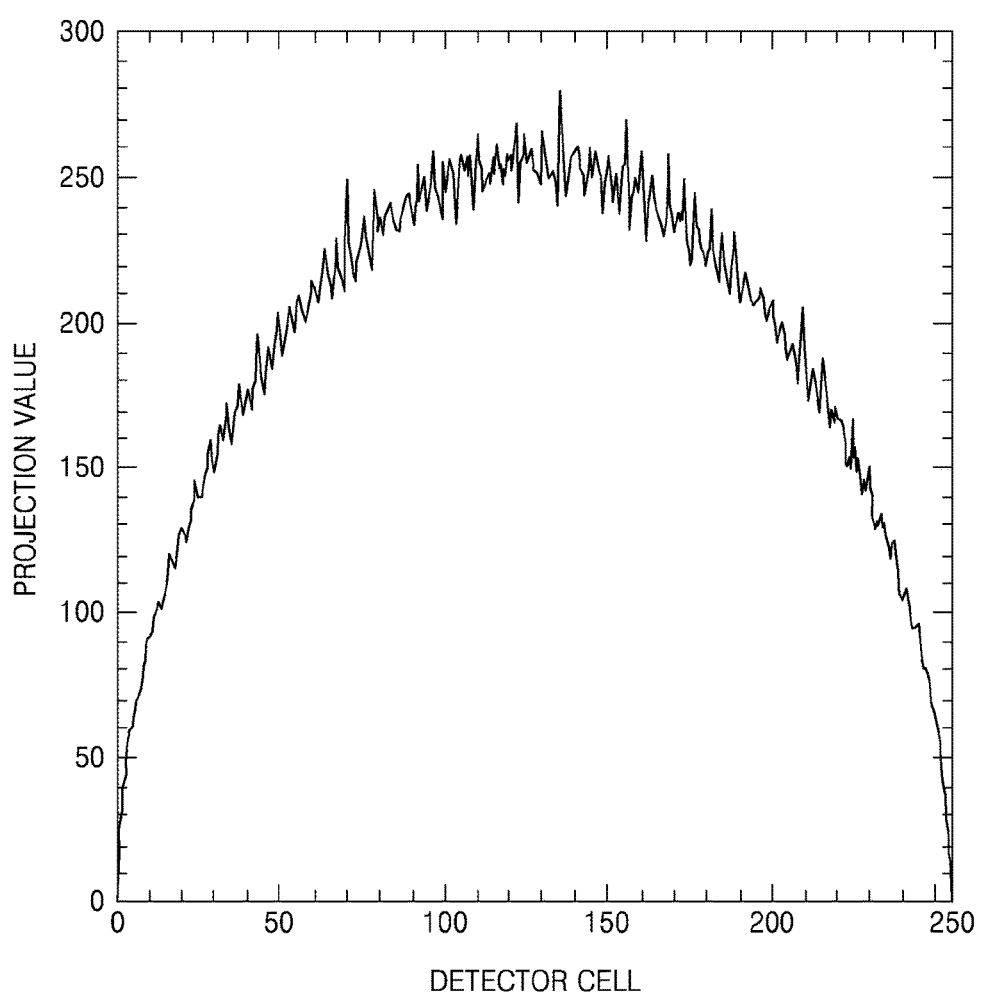
FIG. 4 is a graph illustrating a sinogram acquired according to a second projection method of a uniform disc.

FIG. 4 is a graph illustrating a sonogram according to a second projection method of a uniform disc.

In the first projection method and the second projection method, a contribution of a detector value to a pixel value and a contribution of the pixel value to the detector value are not appropriately reflected, and thus an artifact occurs.

A high frequency component illustrated in FIG. 4 is the artifact.

Figure 5:
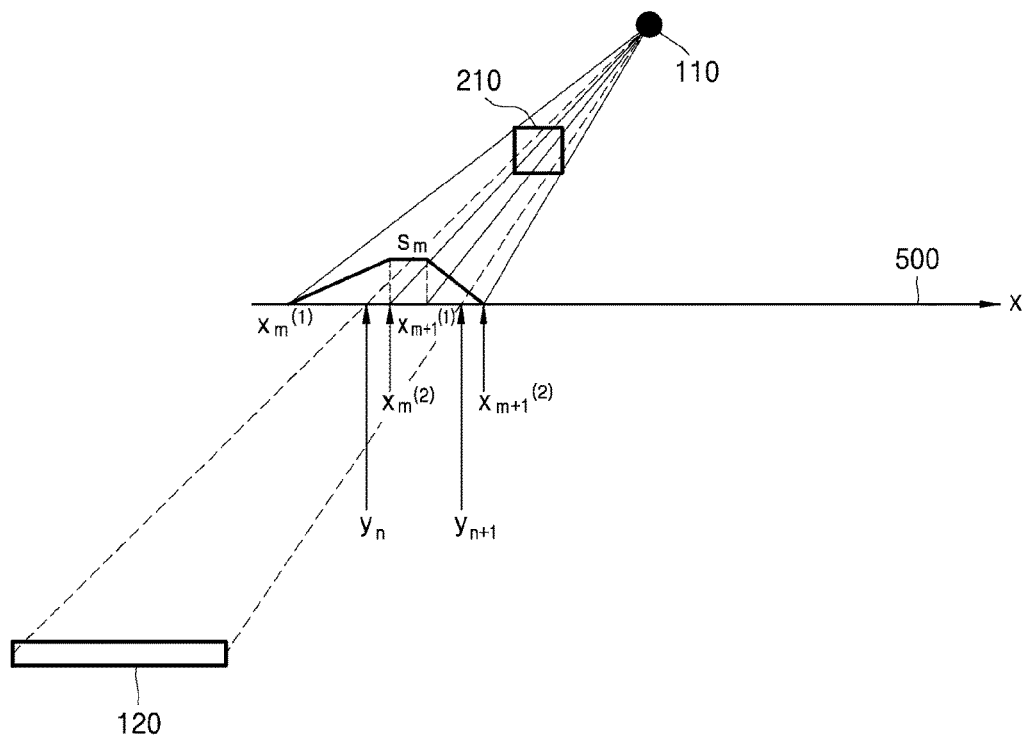
FIG. 5 illustrates a pixel model for performing image processing according to a third projection method.

FIG. 5 illustrates a structure for performing image processing according to a third projection method.

According to the third projection method, a common axis 500 is set, and apexes of the pixel 210 are projected from the source 110 onto the common axis 500. Positions of the apexes projected onto the common axis 500 are respectively $x_m^{(1)}$, $x_m^{(2)}$, $x_{m+1}^{(1)}$, and $x_{m+1}^{(2)}$. $y_n$ and $y_{n+1}$ are points at which a line connecting the source 110 and a boundary of a detector cell 120 and the common axis 500 meet.

The controller 100 may integrate a function, which has a pixel value $s_m$ from $x_m^{(2)}$ to $x_{m+1}^{(1)}$, linearly decreases from $x_m^{(2)}$ to $x_m^{(1)}$, and decreases from $x_{m+1}^{(1)}$ to $x_{m+1}^{(2)}$, from $y_n$ to $y_{n+1}$ to acquire a detector value.

The detector value may be calculated according to the third projection method to acquire a detector value reflecting a distance passing through the pixel 210 from the source 110.

On the contrary, when calculating a pixel value, the pixel value may be calculated from the detector value according to a contrary method.

Also, the common axis 500 may be determined according to relative positions of the source 110, the object 140, and the detection unit 130. For example, x axis that is a horizontal axis or y axis that is a vertical axis may be determined as the common axis 500 according to an angle between the source 110, the object 140, and the detection unit 130. As another example, the common axis 500 may be determined as x axis or the y axis according to an angle between a line connecting the source 110 and the detection unit 130 and the horizontal axis.

Figure 6:
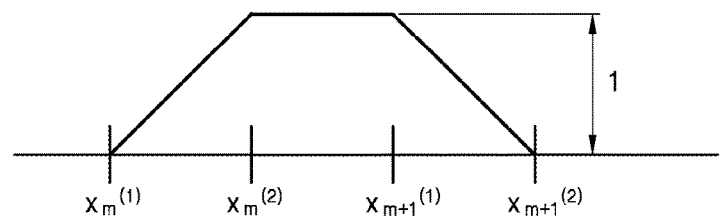
FIG. 6 is a graph illustrating a basis function used in the third projection method.

FIG. 6 is a graph illustrating a basis function used for the third projection method.

As shown in FIG. 5, if a detector value is calculated according to the third projection method, a trapezoidal basis function may be used.

However, if the detector value is calculated according to the third projection method, the number of operations that are performed by the controller 100 increases. Also, a method of changing an area may be changed according to relative positions of the source 110, the pixel 210, and a plurality of detector cells 120, and thus a complexity increases.

Figure 7:
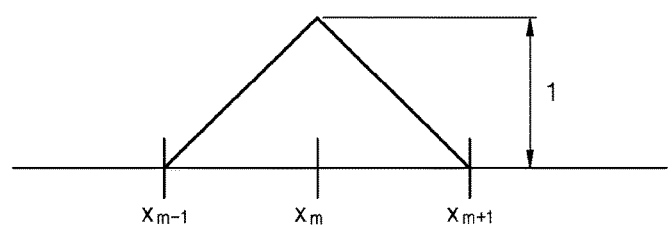
FIG. 7 is a graph illustrating a basis function used in a fourth projection method.

FIG. 7 is a graph illustrating a basis function used for a fourth projection method.

As a detector value is calculated according the third projection method, the number of operations and a complexity increase, and thus a basis function that is a partial linear function as shown in FIG. 7 may be used.

A partial linear model of a pixel value s(x) that is based on a basis function $\beta_m(x)$ may be represented as Equation below.

$$s(x) = \Sigma_m s_m \beta_m(x) \tag{1}$$

Figure 8:
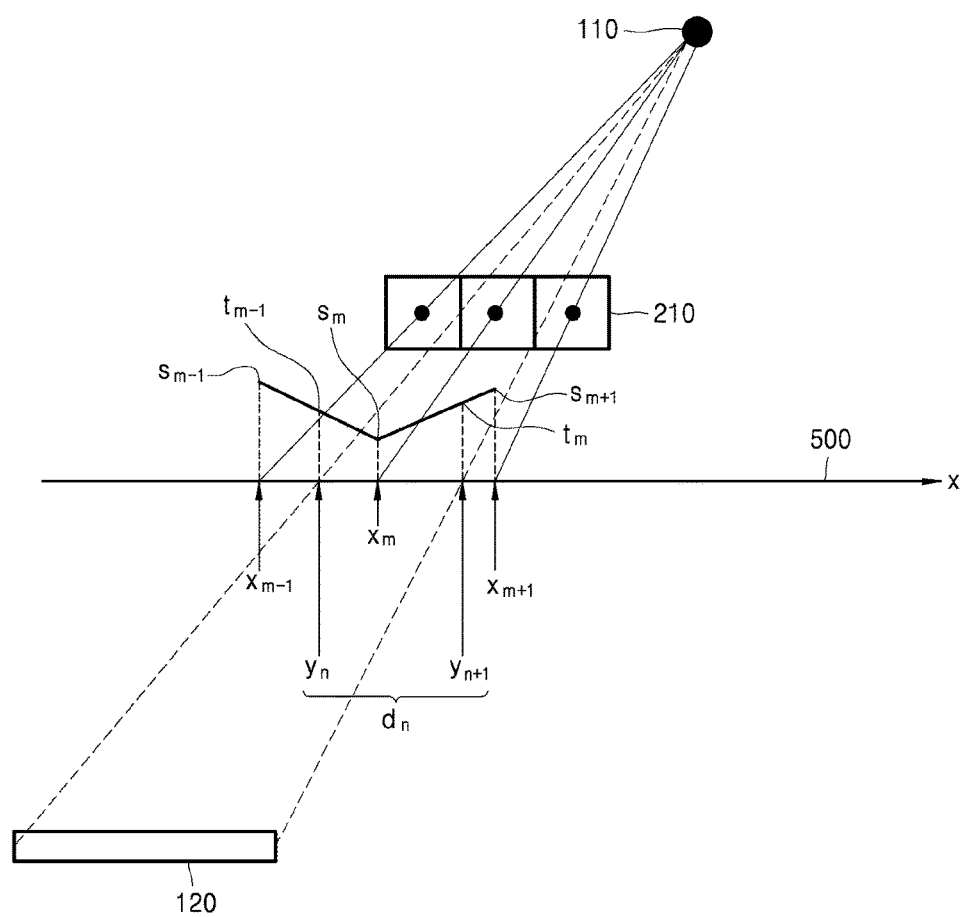
FIG. 8 illustrates a structure for performing a forward projection according to the fourth projection method

FIG. 8 illustrates a structure for performing a forward projection according to the fourth projection method.

Centers of the pixels 210 of the pixel grid 200 are projected onto the common axis 500. In FIG. 8, $x_{m-1}$, $x_m$, and $x_{m+1}$ denote positions of the centers of the pixels 210 projected onto the common axis 500. Pixel values in $x_{m-1}$, $x_m$, and $x_{m+1}$ are $s_{m-1}$, $s_m$, and $s_{m+1}$.

Also, a boundary of the detector cell 120 may be mapped on the common axis 500. Here, the boundary of the detector cell 120 may be mapped on $y_n$ and $y_{n+1}$, that are points at which a line connecting the boundary of the detector cell 120 and the source 110 meets the common axis 500.

Here, the controller 100 of the image processing apparatus may determine a detector value $d_n$ based on a result of projecting the centers of the pixels 210 onto the common axis 500 and a result of mapping the boundary of the detector cell 120 on the common axis 500.

According to an exemplary embodiment of the present invention, the pixel value s(x) may be integrated with respect to an area $[y_n, y_{n+1}]$ to calculate $d_n$. Here, values $t_{m-1}$ and $t_m$ of s(x) in $y_n$ and $y_{n+1}$ may be acquired by a linear interpolation.

Finally, the detector value $d_n$ may be determined by Equation below.

$$d_n = \frac{(x_m - y_n) * \frac{t_{m-1} + s_m}{2} + (y_{n+1} - x_m) * (s_m + t_m)/2}{y_{n+1} + y_n} \tag{2}$$

Also, the present invention may be applied to multidimensional image processing.

Figure 9:
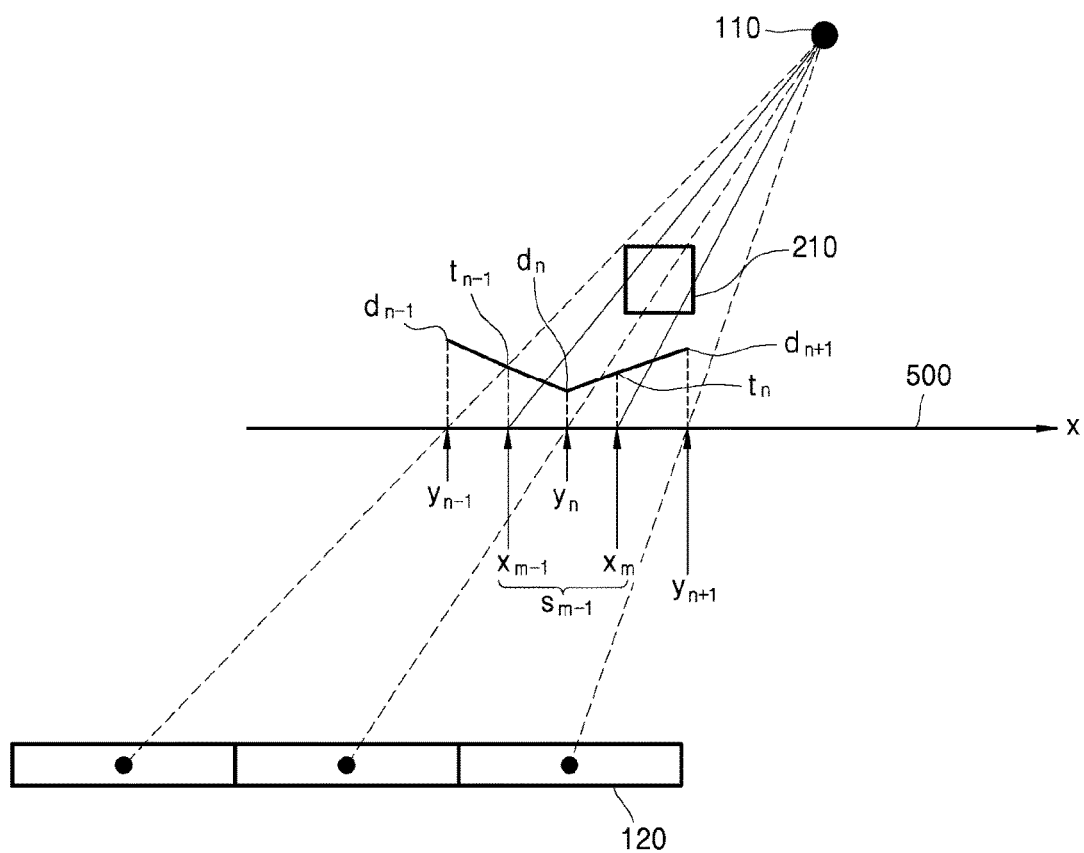
FIG. 9 illustrates a structure for performing a back-projection according to the fourth projection method.

FIG. 9 illustrates a structure for performing a back projection according to the fourth projection method.

Centers of a plurality of detector cells 120 are projected onto the common axis 500. In FIG. 9, $y_{n-1}$, $y_n$, and $y_{n+1}$ denote positions of the centers of the plurality of detector cells 120 projected onto the common axis 500. Pixel values in $y_{n-1}$, $y_n$, and $y_{n+1}$, are $d_{n-1}$, $d_n$, and $d_{n+1}$.

Also, a boundary of a pixel 210 may be mapped on the common axis 500. Here, the boundary of the pixel 210 may be mapped on $x_{m-1}$ and $x_m$ that are points at which an extension line of a line connecting the boundary of the pixel 210 and the source 110 and the common axis 500 meet.

Here, the controller 100 of the image processing apparatus may determine a pixel value $s_{m-1}$ based on a result of projecting the centers of the plurality of detector cells 120 onto the common axis 500 and a result of mapping the boundary of the pixel 210 on the common axis 500.

According to an exemplary embodiment of the present invention, a detector value d(x) may be integrated with respect to $[x_{m-1}, x_m]$ to calculate $s_{m-1}$. Here, values $t_{n-1}$ and $t_n$ of d(x) in $x_{m-1}$ and $x_m$ may be acquired by a linear interpolation.

Finally, the pixel value $s_{m-1}$ may be determined by Equation below.

$$s_{m-1} = \frac{(y_n - x_{m-1}) * \frac{t_{n-1} + d_n}{2} + (x_m - y_n) * (d_n + t_n)/2}{x_m - x_{m-1}} \tag{3}$$

Figure 10:
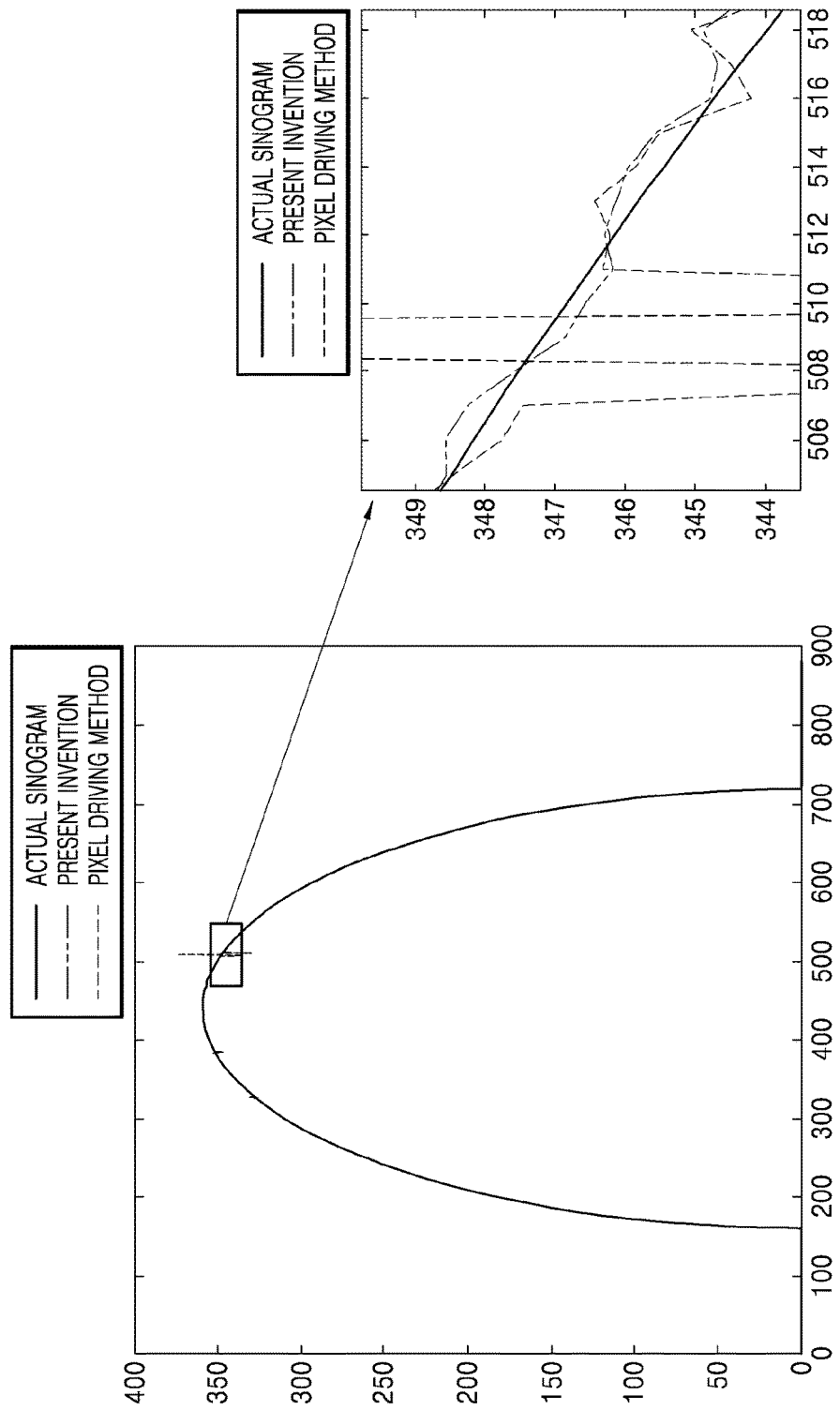
FIG. 10 is a graph illustrating an actual sonogram, a result of the second projection, method, and a result of the fourth projection method in a computer tomography.

FIG. 10 is a graph illustrating an actual sonogram, a result of the second projection method, and a result of the fourth projection method in a computer tomography.

As shown in FIG. 10, a noticeable artifact occurs in an image processing result according to the second projection method, i.e., a pixel-driven method.

However, an image processing result according to the fourth projection method of the present invention may acquire a more similar result to an actual sonogram without a noticeable artifact.

Some of exemplary embodiments may be embodied on a recording medium including a computer-executable program module and a computer-executable command. A computer-readable medium may be an arbitrarily available medium that may be accessed by a computer and may include all of a volatile medium, a nonvolatile medium, a separable type medium, and a non-separable type medium. The computer-readable medium may also include all of a computer storage medium and a communication medium. The computer storage medium may include all of a volatile medium, a nonvolatile medium, a separable medium, and a non-separable medium that are embodied through an arbitrary method or technology for storing information such as a computer-readable command, a data structure, a program module, or other pieces of data. The communication medium includes a computer-readable command, a data structure, a program module, other pieces of data of a modulated data signal such as or the like, or other transmission mechanisms and arbitrary information transmission medial.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. An image processing method of an image processing apparatus including a source configured to generate an electromagnetic wave and a detection unit configured to detect the electromagnetic wave, comprising:
   projecting centers of pixels of a pixel grid onto a preset common axis from the source;
   mapping a boundary of a detector cell comprised in the detection unit on the preset common axis; and
   determining a detector value based on the projecting the centers of the pixels onto the preset common axis and the mapping the boundary of the detector cell on the preset common axis.

2. The image processing method of claim 1, wherein determining the detector value comprises determining the detector value by using equation below:

$$d_n = \frac{(x_m - y_n) * \frac{t_{m-1} + s_m}{2} + (y_{n+1} - x_m) * (s_m + t_m)/2}{y_{n+1} + y_n}$$

wherein $d_n$ denotes the detector value, $x_m$ denotes a position of a center of a pixel projected onto the preset common axis, $s_m$ denotes a pixel value in $x_m$, $y_{n+1}$, and $y_n$ denote positions of the boundary of the detector cell mapped on the preset common axis, and $t_{m-1}$ and $t_m$ denote pixel values corresponding to positions of $y_n$ and $y_{n+1}$.

3. The image processing method of claim 2, wherein the determining the detector value comprises determining a pixel value corresponding a point at which the boundary of the detector cell is mapped on the preset common axis, based on an interpolation.

4. The image processing method of claim 1, further comprising determining the preset common axis according to an angle between a line connecting the source and the detection unit and a horizontal axis.

5. The image processing method of claim 1, wherein determining the detector value comprises determining the detector value based on a partial linear model of a value of a pixel contributing to the detector cell.

6. An image processing method of an image processing apparatus including a source configured to generate an electromagnetic wave and a detection unit configured to detect the electromagnetic wave, comprising:
   projecting centers of detector cells comprised in the detection unit onto a preset common axis toward the source;
   mapping a boundary of a pixel of a pixel grid on the preset common axis; and
   determining a pixel value based on the projecting the centers of the detector cells comprised in the detection unit onto the preset common axis and the mapping the boundary of the pixel on the preset common axis.

7. The image processing method of claim 6, wherein determining the pixel value comprises determining the pixel value by using equation below:

$$s_{m-1} = \frac{(y_n - x_{m-1}) * \frac{t_{n-1} + d_n}{2} + (x_m - y_n) * (d_n + t_n)/2}{x_m - x_{m-1}}$$

wherein $s_{m-1}$ denotes a pixel value, $y_n$ denotes a position of a center of a detector cell projected onto the preset common axis, $d_n$ denotes a detector value in $x_m$, $x_{m-1}$, and $x_m$ denote positions of a boundary of the pixel mapped on the preset common axis, and $t_{n-1}$ and $t_n$ denote detector values corresponding to positions of $x_{m-1}$ and $x_m$.

8. The image processing method of claim 7, wherein the determining the pixel value comprises determining a detector value corresponding to a point at which the boundary of the pixel is mapped on the preset common axis, based on an interpolation.

9. The image processing method of claim 6, further comprising determining the preset common axis according to an angle between a line connecting the source and the detection unit and a horizontal axis.

10. The image processing method of claim 6, wherein determining the pixel value comprises determining the pixel value based on a partial linear model of a value of the detector cell contributing to a pixel.

11. An image processing apparatus comprising:
   a source configured to generate an electromagnetic wave;
   a detection unit comprising a detector cell detecting the electromagnetic wave; and
   a controller configured to project centers of pixels of a pixel grid onto a preset common axis, map a boundary of the detector cell on the preset common axis, and determine a detector value by using the projecting result and the mapping result.

12. The image processing apparatus of claim 11, wherein the controller determines the detector value by using Equation below:

$$d_n = \frac{(x_m - y_n) * \frac{t_{m-1} + s_m}{2} + (y_{n+1} - x_m) * (s_m + t_m)/2}{y_{n+1} + y_n}$$

wherein $d_n$ denotes the detector value, $x_m$ denotes a position of a center of a pixel projected onto the preset common axis, $s_m$ denotes a pixel value in $x_m$, $y_{n+1}$, and $y_n$ denote positions of the boundary of the detector cell mapped on the preset common axis, and $t_{m-1}$ and $t_m$ denote pixel values corresponding to positions of $y_n$ and $y_{n+1}$.

13. The image processing apparatus of claim 12, wherein the controller determines a detector value corresponding to a point at which the boundary of the detector cell is mapped on the preset common axis, based on an interpolation.

14. The image processing apparatus of claim 11, wherein the controller determines the preset common axis according to an angle between a line connecting the source and the detection unit and a horizontal axis.

15. The image processing apparatus of claim 11, wherein the controller determines the detector value based on a partial linear model of a value of a pixel contributing to the detector cell.

16. An image processing apparatus comprising:
a source configured to generate an electromagnetic wave;
a detection unit comprising a plurality of detectors cells detecting the electromagnetic wave; and
a controller configured to project centers of detector cells among the plurality of detection cells onto a preset common axis, map a boundary of a pixel of a pixel grid on the preset common axis, and determine a pixel value by using the projection result and the mapping result.

17. The image processing apparatus of claim 16, wherein the controller determines the pixel value by using Equation below:

$$s_{m-1} = \frac{(y_n - x_{m-1}) * \frac{t_{n-1} + d_n}{2} + (x_m - y_n) * (d_n + t_n)/2}{x_m - x_{m-1}}$$

wherein $s_{m-1}$ denotes a pixel value, $y_n$ denotes a position of a center of a detector cell projected onto the preset common axis, $d_n$ denotes a detector value in $y_n$, $x_{m-1}$, and $x_m$ denote positions of a boundary of the pixel mapped on the preset common axis, and $t_{n-1}$ and $t_n$ denote detector values corresponding to positions of $x_{m-1}$ and $x_m$.

18. The image processing apparatus of claim 17, wherein the controller determines a detector value corresponding to a point at which the boundary of the pixel is mapped on the common axis, based on an interpolation.

19. The image processing apparatus of claim 16, wherein the controller determines the preset common axis according to an angle between a line connecting the source and the detection unit and a horizontal axis.

20. The image processing apparatus of claim 16, wherein the controller determines the pixel value based on a partial linear model of a value of the detector cell contributing to a pixel.

21. A non-transitory computer-readable recording medium having recorded thereon a program executable by a computer for performing the image processing method of claim 1.

* * * * *